(12) United States Patent
Kamal et al.

(10) Patent No.: US 7,173,026 B2
(45) Date of Patent: Feb. 6, 2007

(54) PYRROLO [2,1-C][1,4]BENZODIAZEPINE-ANTHRAQUINONE CONJUGATES USEFUL AS ANTITUMOUR AGENTS

(75) Inventors: Ahmed Kamal, Hyderabad (IN); Gollapalli B. Khanna Ramesh, Hyderabad (IN); Ramu Rondla, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 11/024,240

(22) Filed: Dec. 27, 2004

(65) Prior Publication Data

US 2006/0142272 A1 Jun. 29, 2006

(51) Int. Cl.
C07D 487/04 (2006.01)
A61K 31/551 (2006.01)
A61P 35/00 (2006.01)

(52) U.S. Cl. ..................... 514/220; 540/496
(58) Field of Classification Search ............... 540/496; 514/220
See application file for complete search history.

(56) References Cited

OTHER PUBLICATIONS

Kunimoto, S., et al., "Mazethramycin, A New Member of Anthramycin Group Antibiotics", The Journal of Antibiotics, Jun. 1980, pp. 665-667.
Thurston, D.E., et al., "Synthesis of a Novel GC-Specific Covalent-Binding DNA Affinity-Cleavage Agent Based on Pyrrolobenzodiazepines (PDBs)", Chemical Communications, 1996, pp. 563-565.
Monks, A., et al., "Feasibility of a High-Flux Anticancer Drug Screen Using a Diverse Panel of Cultured Human Tumor Cell Lines", Journal of the National Cancer Institute, Jun. 5, 1991, vol. 83, No. 11, pp. 757-766.
Damayanthi, Y., et al., "Design and Synthesis of Novel Pyrrolo[2,1-c][1,4]benzodiazepine-Lexitropsin Conjugates", Journal of Organic Chemistry, Jan. 8, 1999, vol. 64, No. 1, pp. 42290-42292.
Hurley, L.H., et al., "Pyrrolo(1,4)benzodiazepine Antitumor Antibiotics In Vitro Interaction of Anthramycin, Sibiromycin and Tomaymycin With DNA Using Specifically Radiolabelled Molecules", Biochemica et Biophysica Acta, Apr. 4, 1977, vol. 475, No. 3, pp. 521-535.

Kamal, A., et al., "Design and Synthesis of C-8 Linked Pyrrolobenzodiazepine-Naphthalimide Hybrids as Anti-Tumour Agents", Bioorganic & Medicinal Chemistry Letters, 2002, vol. 12, pp. 1933-1935.
Kamal, A., et al., "Design, Synthesis, and Evaluation of New Noncross-Linking Pyrrolobenzodiazepine Dimers with Efficient DNA Binding Ability and Potent Antitumor Activity," Journal of Medicinal Chemistry, Oct. 10, 2002, vol. 45, No. 21, pp. 4679-4688.
Kaplan, D.J., et al., "Anthramycin Binding to Deoxyribonucleic Acid-Mitomycin C Complexes. Evidence for Drug-Induced Deoxyribonucleic Acid Conformational Change and Cooperativity in Mitomycin C Binding," Biochemistry, Dec. 22, 1981, vol. 20, No. 26, pp. 7572-7580.
Collier, D.A., et al., "Synthesis, Molecular Modeling, DNA Binding, and Antitumor Properties of Some Substituted Amidoanthraquinones," Journal of Medicinal Chemistry, Apr. 1988, vol. 31, No. 4, pp. 847-857.
Thurston, D.E., et al., "O-Debenzylation of a Pyrrolo[2,1-c][1,4]benzodiazepine in the Presence of a Carbinolamine Functionality: Synthesis of DC-81," Synthesis, Jan. 1990, No. 1, pp. 81-84.
Kamal, A. et al., "Pyrrolo[2,1-c][1,4]benzodiazepine-anthraquinone conjugates. Synthesis, DNA binding and cytotoxity," Bioorganic & Medicinal Chemistry Letters 2004, vol. 14, pp. 4907-4909.
Kohn K.W. et al., C. L. J. Mol. Biol. 1970, vol. 91, p. 551.
Gregson, S.J. et al., J. Med. Chem. 2001, vol. 44, p. 737.

*Primary Examiner*—Bruck Kifle
(74) *Attorney, Agent, or Firm*—Darby & Darby

(57) ABSTRACT

The present invention relates to synthesis of pyrrolo[2,1-c][1,4]benzodiazepine-anthraquinone hybrids (V) wherein n=3,4; R=H, OH

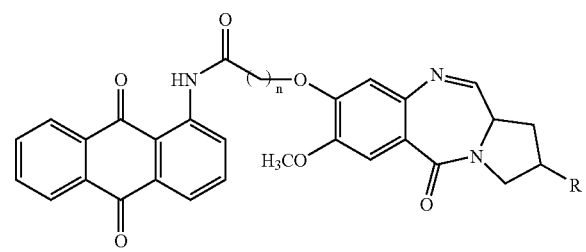

and to their use as antitumour agents.

14 Claims, No Drawings

PYRROLO [2,1-C][1,4]BENZODIAZEPINE-ANTHRAQUINONE CONJUGATES USEFUL AS ANTITUMOUR AGENTS

FIELD OF THE INVENTION

The present invention relates to pyrrolo[2,1-c][1,4]benzodiazepine-anthraquinone hybrids useful as potential antitumour agents. The present invention particularly relates to the synthesis of pyrrolo[2,1-c][1,4]benzodiazepine-anthraquinone hybrids as useful anticancer agents. The structural formula of novel pyrrolo[2,1-c][1,4]benzodiazepine-anthraquinone hybrids (V) is as follows, wherein n=3,4; R=H, OH.

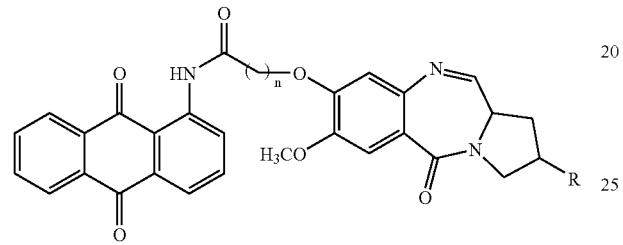

V

The present invention also relates to a process a process for the preparation of such hybrids and to the use thereof as anti-tumour agents.

BACKGROUND OF THE INVENTION

Pyrrolo[2,1-c][1,4]benzodiazepines are a family of DNA interactive antitumour antibiotics derived from *streptomyces* species. Examples of naturally occurring pyrrolo[2,1-c][1,4]benzodiazepines include anthramycin, tomaymycin, sibiromycin and DC-81. These compounds show their biological activity through covalent binding via their N10-C11 imine/carbinol amine moiety to the C2-amine position of a guanine residue within the minor groove of DNA giving rise to the preference for pu-G-pu sequences. (Kunimoto, S.; Masuda, T.; Kanbayashi, N.; Hamada, M.; Naganawa, H.; Miyamoto, M.; Takeuchi, T and Unezawa, H, J. Antibiot., 1980, 33, 665.; Kohn, K. W. and Speous, C. L. J. Mol. Biol., 1970, 91, 551.; Hurley, L. H.; Gairpla, C. and Zmijewski, M. Biochem. Biophy. Acta., 1977, 475, 521.; Kaplan, D. J. and Hurley, L. H. Biochemistry, 1981, 20, 7572.) The molecules have a right-handed twist, when viewed from the C-ring towards the A-ring. This enables the PBD to mirror the curvature of B-form DNA and maintain isohelical contact with the walls and floor of the minor groove.

In the last few years a growing interest has been shown in the development of new pyrrolo[2,1-c][1,4]benzodiazepine hybrids. Many PBD conjugates have been synthesized and investigated for their anticancer activity. (Thurston, D. E.; Morris, S. J.; Hartley, J. A. Chem. Commun. 1996, 563.; Damayanthi, Y.; Reddy, B. S. P.; Lown, J. W. J. Org. Chem. 1999, 64, 290; Kamal, A.; Reddy, B. S. N.; Reddy, G. S. K., Ramesh, G Bioorg. Med. Chem. Lett. 2002, 12, 1933). Recently C-8 linked PBD dimers with C2/C2 exounsaturation have been designed and synthesized (Gregson, S. J.; Howard, P. W.; Hartley, J. A.; Brooks, N. A.; Adam, L. J.; Jenkins, T. C.; Kelland, L. R. and Thurston, D. E., J. Med. Chem. 2001, 44, 737).

Recently, a non cross-linking mixed imine-amide PBD dimers have been synthesized that have significant DNA binding ability and potent antitumor activity (Kamal, A.; Ramesh, G.; Laxman, N.; Ramulu, P.; Srinivas, O.; Neelima, K., Kondapi, A. K.; Srinu, V. B.; Nagarajaram, H. M. J. Med. Chem. 2002, 45, 4679).

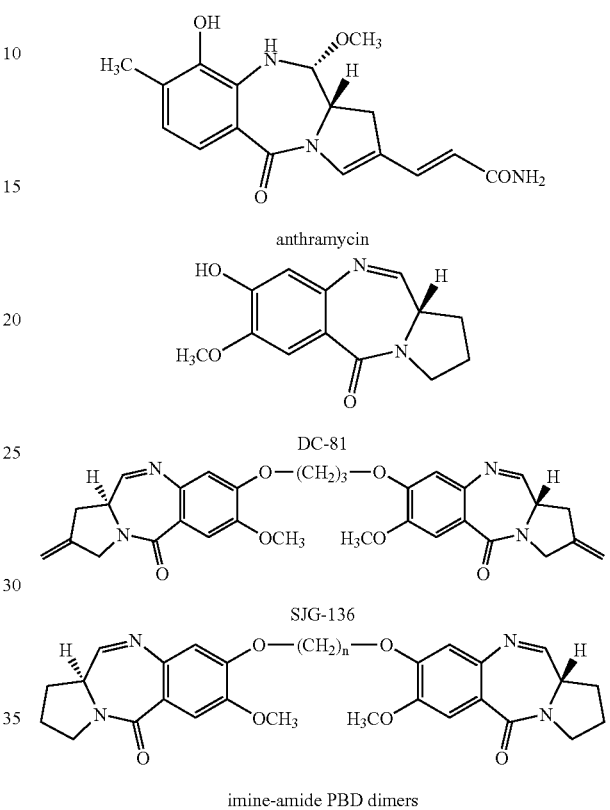

OBJECTS OF THE INVENTION

The main object of the invention is to provide new pyrrolo[2,1-c][1,4]benzodiazepines useful as anticancer agents.

Another object of the invention is to provide a process for preparing novel pyrrolo[2,1-c][1,4]benzodiazepines useful as antitumor agents.

SUMMARY OF THE INVENTION

Accordingly, the present invention provides novel pyrrolo[2,1-c][1,4]benzodiazepine of formula V where n=3, 4 R=H, OH

V

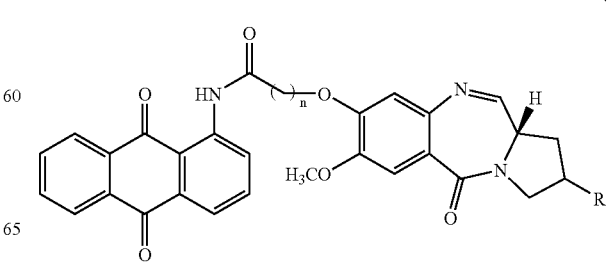

In one embodiment of the invention, the compound of formula V is selected from the group consisting of
(a) 7-Methoxy-8-[N-(9,10-dihydro-9,10-dioxo-1-anthracenyl)-propane-3-carboxamide]-oxy-(11aS)-1,2,3,11a tetrahydro-5H-pyrrolo[2,1-c][1,4]benzodiazepin-5-one;
(b) 7-Methoxy-8-[N-(9,10-dihydro-9,10-dioxo-1-anthracenyl)-propane-3 -carboxamide]-oxy-(4R)-hydroxy-(11aS)-1,2,3,11atetrahydro-5H-pyrrolo[2,1-C][1,4]benzodiazepine-5-one,
(c) 7-Methoxy-8-[N-(9,10-dihydro-9,10-dioxo-1-anthracenyl)-butane-4-carboxamide]-oxy-(11aS)-1,2,3,11a tetrahydro-5H-pyrrolo [2,1-c][1,4]benzodiazepin-5-one; and
(d) 7-Methoxy-8-[N-(9,10-dihydro-9,10-dioxo-1-anthracenyl)-butane-4-carboxamide]-oxy-(4R)-hydroxy-(11aS)-1,2,3,11a tetrahydro-5H-pyrrolo[2,1-C][1,4]benzodiazepine-5-one.

The present invention also provides a process for the preparation of pyrrolo[2,1-c][1,4]benzodiazepines of formula V wherein n is 3–4 and R is H, OH,

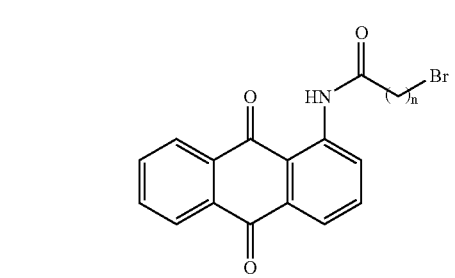

V the process comprising:

reacting N-(9,10-dihydro-9,10-dioxo-1-anthracenyl)-1-bromo-alkanamide of formula I with (2S)-N-[4-hydroxy-5-methoxy-2-nitrobenzoyl]pyrrolidine-2-carboxaldehyde diethyl thioacetal of formula II in an aprotic water miscible organic solvent in the presence of a mild inorganic base

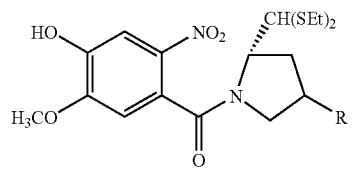

I

II and isolating 2S-N-{4-[N-(9,10-dihydro-9,10-dioxo-1-anthracenyl)-alkane-3-carboxamide]-oxy-5-methoxy-2-nitrobenzoyl}pyrrolidine-2-carbaxaldehyde diethyl thioacetal of formula III so obtained;

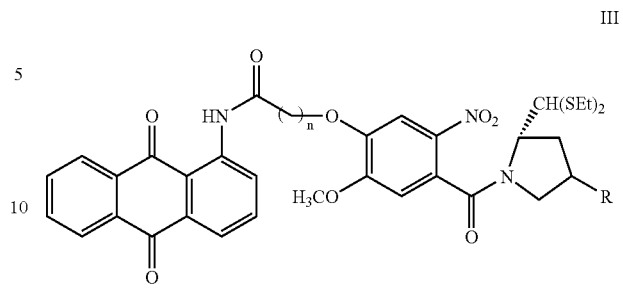

III (b) reducing the thioacetal of formula III in presence of organic solvent and isolating 2S-N-{4-[N-(9,10-dihydro-9,10-dioxo-1-anthracenyl)-alkane-3-carboxamide]-oxy-5-methoxy-2-aminobenzoyl}pyrrolidine-2-carbaxaldehyde diethyl thioacetal of formula IV so obtained;

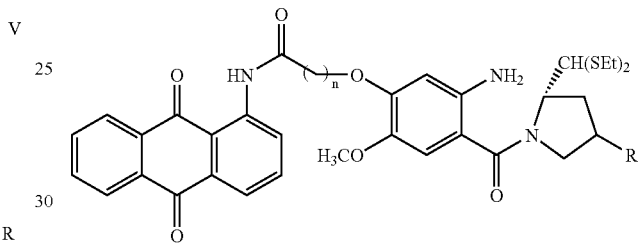

IV (c) reacting the amino thioacetal of formula IV with a deprotecting agent to give the pyrrol[2,1-c][1,4]benzodiazepine of formula V wherein n and R are as stated above.

In one embodiment of the invention, the compound of formula I is reacted with the compound of formula II at refluxing temperature and for a period of 48 h.

In another embodiment of the invention, the thioacetal of formula III is reduced using $SnCl_2 \cdot 2H_2O$ and in presence of an organic solvent and at reflux temperature.

In another embodiment of the invention, the organic solvent in step (a) comprises acetone.

In yet another embodiment of the invention, the base in step (a) comprises $K_2CO_3$.

In another embodiment of the invention, step (b) is carried out in methanol solvent.

The present invention also provides a method for the treatment of tumours in a subject, comprising administering to the subject a pharmaceutically effective amount of a pyrrolo[2,1-c][1,4]benzodiazepines of formula V wherein n is 3–4 and R is H, OH,

V

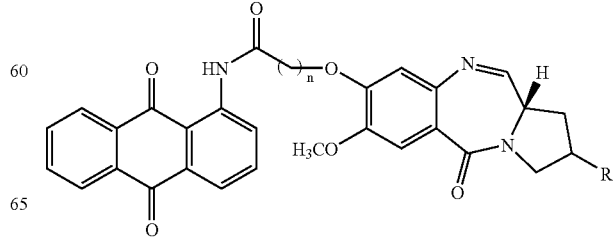

In one embodiment of the invention, the subject is a mammal.

In another embodiment of the invention, the subject is a human being.

In another embodiment of the invention, the tumour is a human cancer cell line selected from the group consisting of HT-29, HCT-15, A-549, HOP-62 and SiHA.

DETAILED DESCRIPTION OF THE INVENTION

The present invention provides a novel pyrrolo[2,1-c][1,4]benzodiazepine of formula V wherein n is 3–4 and R is H, OH,

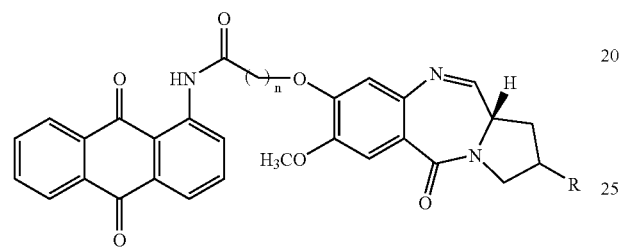

V

The precursors, N-9,10-dihydro-9,10-dioxo-1-anthracenyl)-1-bromo-alkanamide of formula I (Collier, D. A.; Neidle, S.; J. Med. Chem., 1988, 847) and (2S)-N-[4-hydroxy-5-methoxy-2-nitrobenzoyl]pyrrolidine-2-carboxaldehyde diethyl thio-acetal of formula II (Thurston, D. E.; Murthy, V. S.; Langley, D. R.; Jones, G.; B. Synthesis, 1990, 81) have been prepared by literature methods.

Some representative compounds of formula V of present invention are given below:

1. 7-Methoxy-8-[N-(9,10-dihydro-9,10-dioxo-1-anthracenyl)-propane-3-carboxamide]-oxy-(11aS)-1,2,3,11a tetrahydro-5H-pyrrolo [2,1-c][1,4]benzodiazepin-5-one
2. 7-Methoxy-8-[N-(9,10-dihydro-9,10-dioxo-1-anthracenyl)-propane-3-carboxamide]-oxy-(4R)-hydroxy-(11aS)-1,2,3,11atetrahydro-5H-pyrrolo[2,1-C][1,4]benzodiazepine-5-one
3. 7-Methoxy-8-[N-(9,10-dihydro-9,10-dioxo-1-anthracenyl)-butane-4-carboxamide]-oxy-(11aS)-1,2,3,11a tetrahydro-5H-pyrrolo [2,1-c][1,4]benzodiazepin-5-one
4. 7-Methoxy-8-[N-(9,10-dihydro-9,10-dioxo-1-anthracenyl)-butane-4-carboxamide]-oxy-(4R)-hydroxy-(11aS)-1,2,3,11a tetrahydro-5H-pyrrolo[2,1-C][1,4]benzodiazepine-5one The pyrrolo[2,1-c][1,4]benzodiazepines of formula V wherein n is 3–4 and R is H, OH are prepared by, reacting N-(9,10-dihydro-9,10-dioxo-1-anthracenyl)-1-bromo-alkanamide of formula I with (2S)-N-[4-hydroxy-5-methoxy-2-nitrobenzoyl]pyrrolidine-2-carboxaldehyde diethyl thioacetal of formula II in an aprotic water miscible organic solvent in the presence of a mild inorganic base

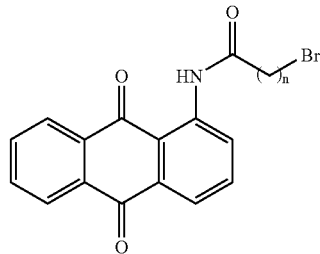

I

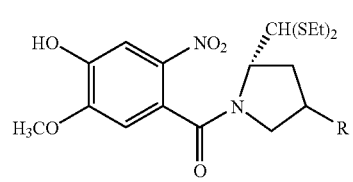

II and isolating 2S-N-{4-[N-(9,10-dihydro-9,10-dioxo-1-anthracenyl)-alkane-3-carboxamide]-oxy-5-methoxy-2-nitrobenzoyl}pyrrolidine-2-carbaxaldehyde diethyl thioacetal of formula III so obtained.

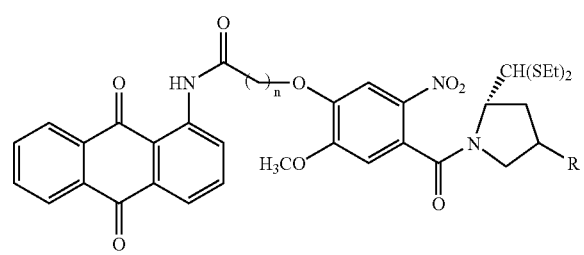

III

The thioacetal of formula III is reduced with with $SnCl_2.2H_2O$ in presence of organic solvent and isolating 2S-N-{4-[N-(9,10-dihydro-9,10-dioxo-1-anthracenyl)-alkane-3-carboxamide]-oxy-5-methoxy-2-aminobenzoyl}pyrrolidine-2-carbaxaldehyde diethyl thioacetal of formula IV so obtained.

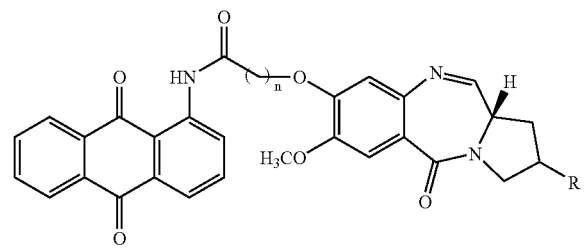

V

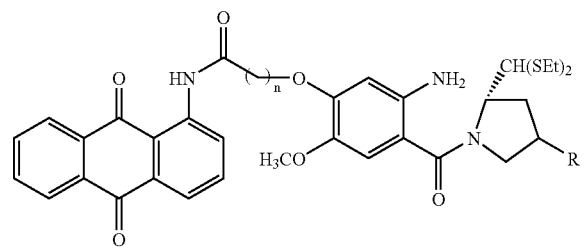

IV

The amino thioacetal of formula IV is reacted with a known deprotecting agent in a conventional manner to give the pyrrol[2,1-c][1,4]benzodiazepine of formula V wherein n and R are as stated above.

In the process, the compound of formula I is reacted with the compound of formula II at refluxing temperature and for a period of 48 h. The thioacetal of formula III is reduced using SnCl$_2$.2H$_2$O and in presence of an organic solvent and at reflux temperature. The organic solvent in step (a) of the process is preferably acetone and the base comprises K$_2$CO$_3$.

Reduction in step (b) is carried out in methanol solvent.

The present invention also provides a method for the treatment of tumours in a subject, comprising administering to the subject a pharmaceutically effective amount of a pyrrolo[2,1-c][1,4]benzodiazepines of formula V wherein n is 3–4 and R is H, OH,

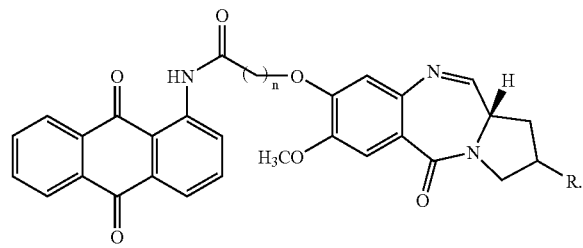

V

The subject is a mammal such as a human being. The tumour is a human cancer cell line selected from the group consisting of HT-29, HCT-15, A-549, HOP-62 and SiHA.

These new analogues of pyrrlo [2,1-c][1,4]benzodiazepine hybrids have shown promising anticancer activity in various cell lines. The molecules synthesized are of immense biological significance with potential sequence selective DNA-binding property. This resulted in design and synthesis of new congeners as shown in scheme-I below wherein:

The ether linkage is at C-8 position of DC-81 intermediates with Anthraquinone moiety.

The reaction mixture is refluxed for a period of 24–48 h

C-8 linked PBD hybrids are synthesised.

Purification is effected by column chromatography using different solvents like ethyl acetate, hexane, dichloromethane and methanol.

Scheme I

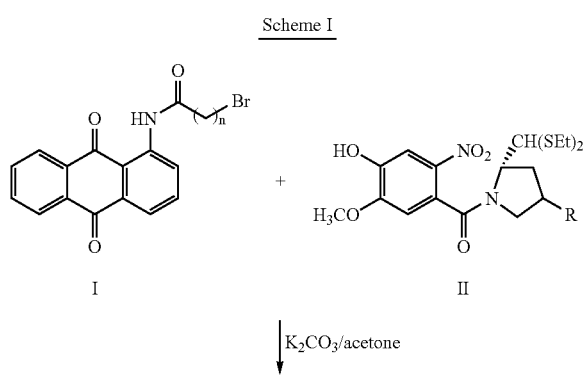

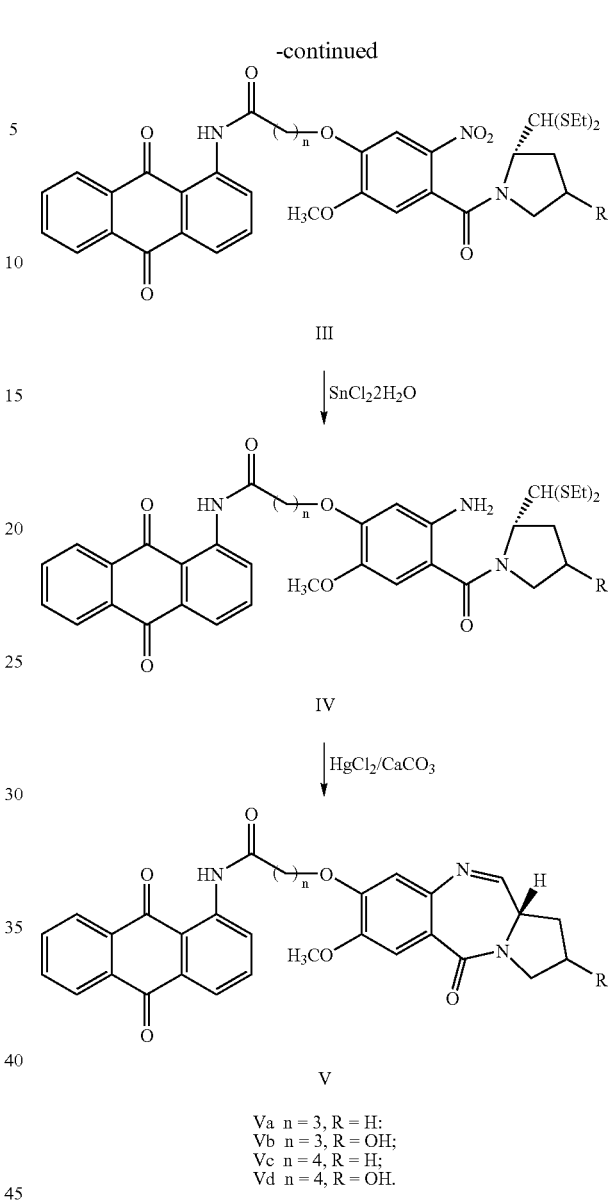

Va n = 3, R = H;
Vb n = 3, R = OH;
Vc n = 4, R = H;
Vd n = 4, R = OH.

The following examples are given by way of illustration and therefore should not be construed to the present limit of the scope of invention.

EXAMPLE 1

To a solution of (2S)-N-[4-hydroxy-5-methoxy-2-nitrobenzoyl]pyrrolidine-2-carboxaldehyde diethyl thioacetal (400 mg, 1 m.mol) of formula II in acetone, anhydrous K$_2$CO$_3$ (553 mg, 4 m.mol) and N-(9,10-dihydro-9,10-dioxo-1-anthracenyl)-1-bromo-propanamide (372 mg, 1 m.mg) of formula I were added and mixture refluxed for 48 h. After completion of reaction K$_2$CO$_3$ was removed by filtration and the solvent was evaporated under reduced pressure, and purified by column chromatography to provide compound III.

$^1$HNMR (CDCl$_3$) 1.21–1.38 (m, 6H), 1.53–2.42 (m, 6H), 2.62–2.81 (m, 6H), 3.10–3.28 (m, 2H), 3.91 (s, 3H), 4.25 (m, 2H), 4.65 (m, 1H), 4.80 (d, 1H), 6.74 (s, 1H), 7.68 (s, 1H), 7.71–7.85 (m, 3H), 8.0 (d, 1H), 8.20–8.30 (m, 2H), 9.15 (d, 1H), 12.38 (bs, 1H).

To a solution of 2S-N-{4-[N-(9,10-dihydro-9,10-dioxo-1-anthracenyl)-propane-3-carboxamide]-oxy-5-methoxy-2-nitrobenzoyl}pyrrolidine-2-carbaxaldehyde diethyl thioacetal (692 mg, 1 m.mol) of formula III in methanol $SnCl_2.2H_2O$ (1128 mg, 5 m.mol) was added and mixture was refluxed till TLC indicated completion of reaction. Methanol was evaporated and 10% $NaHCO_3$ solution was added. The aqueous layer was extracted with ethyl acetate, the combined organic phases were dried over $Na_2SO_4$ and evaporated under vacuum to provide a amino thioacetal (IV) and directly used in the next step.

A solution of compound IV (662 mg, 1 m.mol) $HgCl_2$ (624 mg, 2.3 m.mol) and $CaCO_3$ (250 mg, 2.5 mg) in $CH_3CN$—$H_2O$ (4:1) was stirred at room temperature till TLC indicated complete consumption of starting material. Reaction mixture was diluted with ethyl acetate and filtered through a celite bed. Organic layer was concentrated, dried and purified by column chromatography to give the compound V.

$^1$HNMR ($CDCl_3$) 2.05 (m, 2H), 2.20–2.40 (m, 4H), 2.81 (m, 2H), 3.50–3.81 (m, 3H), 3.91 (s, 3H), 4.15–4.26 (m, 2H), 6.76 (s, 1H), 7.42 (s, 1H), 7.55 (d, 1), 7.80 (m, 3H), 8.0 (d, 1H), 8.2–8.3 (m, 2H), 9.15 (d, 1H), 12.38 (bs, 1H).

EXAMPLE 2

To a solution of (2S)-N-[4-hydroxy-5-methoxy-2-nitrobenzoyl]pyrrolidine-2-carboxaldehyde diethyl thioacetal (400 mg, 1 m.mol) of formula II in acetone were added anhydrous $K_2CO_3$ (553 mg, 4 m.mol) and N-(9,10-dihydro-9,10-dioxo-1-anthracenyl)-1-bromo-butanamide (386 mg, 1 m.mg) of formula I and the mixture was refluxed for 48 h. $K_2CO_3$ was removed by filtration and then the solvent was evaporated under reduced pressure, purification by column chromatography afforded compound III.

$^1$HNMR ($CDCl_3$) 1.21–1.42 (m, 6H), 1.60–2.40 (m, 8H), 2.62–2.85 (m, 6H), 3.15–3.30 (m, 2H), 3.95 (s, 3H), 4.10–4.25 (m, 2H), 4.65 (m, 1H), 4.84 (d, 1H), 6.78 (s, 1H), 7.68 (s, 1), 7.75–7.90 (m, 3H), 8.05 (d, 1H), 8.20–8.35 (m, 2H), 9.15 (d, 1H), 12.38 (bs, 1H).

To a solution of 2S-N-{4-[N-(9,10-dihydro-9,10-dioxo-1-anthracenyl)-butane-3-carboxamide]-oxy-5-methoxy-2-nitrobenzoyl}pyrrolidine-2-carbaxaldehyde diethyl thioacetal (706 mg, 1 mmol) of formula III in methanol, $SnCl_2.2H_2O$ (1128 mg, 5 mmol) was added. The mixture was refluxed till TLC indicated completion of reaction. Methanol was evaporated and 10% $NaHCO_3$ solution was added. Aqueous layer was extracted with ethyl acetate. Combined organic phases was dried over $Na_2SO_4$ and evaporated under vacuum to obtain amino thioacetal (IV) which was directly used in the next step.

A solution of IV (676 mg, 1 mmol) $HgCl_2$ (624 mg, 2.3 mmol) and $CaCO_3$ (250 mg, 2.5 mg) in $CH_3CN$—$H_2O$ (4:1) was stirred at room temperature until the TLC indicated complete loss of the starting material. The reaction mixture was diluted with ethyl acetate and filtered through a celite bed. The organic layer was concentrated, dried and purified by column chromatography to give the compound V.

$^1$HNMR ($CDCl_3$) 1.85–2.40 (m, 8H), 2.60–2.78 (m, 2H), 3.51–3.80 (m, 3H), 3.93 (s, 3H), 4.15–4.20 (m, 2H), 6.78 (s, 1H), 7.42 (s, 1H), 7.60 (d, 1H), 7.65–7.83 (m, 3H), 8.0 (d, 1H), 8.2–8.25 (m, 2H), 9.15 (d, 1H), 12.38 (bs, 1H).

Biological Activity

In vitro cytotoxicity against human cancer cell lines: The human cancer cell lines procured from National Cancer Institute, Frederick, U.S.A or National Center for Cell Science; Pune, India. were used in present study. Cells were grown in tissue culture flasks in complete growth medium (RPMI-1640 medium with 2 mM glutamine, 100 µg/ml streptomycin, pH 7.4, sterilized by filtration and supplemented with 10% fetal calf serum and 100 units/ml penicillin before use) at 37° C. in an atmosphere of 5% $CO_2$ and 90% relative humidity in a carbon dioxide incubator. The cells at subconfluent stage were harvested from the flask by treatment with trypsin (0.5% in PBS containing 0.02% EDTA) for determination of cytotoxicity. Cells with viability of more than 98% as determined by trypan blue exclusion were used for assay. Cell suspension of the required cell density were prepared in complete growth medium with gentamycin (50 µg/ml) for determination of cytotoxicity.

Stock solutions of (2×10-2 M of test material were prepared in DMSO (Dimethyl sulphoxide). The stock solutions were serially diluted with complete growth medium containing 50 µg/ml of gentamycin to obtain working test solutions of required concentrations.

In vitro cytotoxicity against human cancer cell lines was determined (Monks, A., Scudiero, D., Skehan, P., Shoemaker R., Paull, K., Vistica, D., Hose, C., Langley, j., Cronise, P., Vaigro-Wolff, A., Gray-Goodrich, M., Campbell, H., Mayo, J and Boyd m.J. Natl. Cancer Inst., 1991, 83, 757–766) using 96-well tissue culture plates. 100 µl of cell suspension was added to each well of the 96-well tissue culture plate. The cells were incubated for 24 hours. Test materials in complete growth medium (100 µl) were added after 24 hours incubation to the wells containing cell suspension. The plates were further incubated for 48 hours (at 37° C. in an atmosphere of 5% and 90% relative humidity in a carbon dioxide incubator) after addition of test material and then the cell growth was stopped by gently layering trichloroacetic acid (TCA, 50 µl, 50%) on top of the medium in all the wells. The plates were incubated at 4° C. for one hour to fix the cells attached to the bottom of the wells. The liquid of all the wells was gently pipetted out and discarded. The plates were washed five times with distilled water to remove TCA, growth medium low molecular weight metabolites, serum proteins etc and air-dried. Cell growth was measured by staining with sulforhodamine B dye (Skehan et al., 1990). The adsorbed dye was dissolved in Tris-Buffer (100 m l, 0.01M, pH 10.4) and plates were gently stirred for 5 minutes on a mechanical stirrer. The optical density was recorded on ELISA reader at 540 nm.

The cell growth was calculated by subtracting mean OD value of respective blank from the mean OD value of experimental set. Percent growth in presence of test material was calculated considering the growth in absence of any test material as 100% and in turn percent growth inhibition in presence of test material will be calculated.

Cytotoxicity: Compounds Va and Vc were evaluated for the primary anticancer activity

TABLE 1

The percentage growth inhibition data for compound Va

| Concentration (mol/L) | Cell lines HT-29 | HCT-15 | A-549 | HOP-62 | SiHa |
|---|---|---|---|---|---|
| 10-6 | 68 | 59 | 47 | 74 | 41 |
| 10-5 | 86 | 66 | 27 | 90 | 52 |
| 10-4 | 93 | n.t. | 93 | n.t. | 57 |

TABLE 2

The percentage growth inhibition data for compound Vc

| Concentration (mol/L) | Cell lines HT-29 | HCT-15 | A-549 | HOP-62 | SiHa |
|---|---|---|---|---|---|
| 10-6 | 73 | 61 | 56 | 73 | 40 |
| 10-5 | 87 | 82 | 10 | 97 | 49 |
| 10-4 | 93 | n.t. | 93 | n.t. | 73 | n.t. not tested

What is claimed is:

1. A compound of formula V

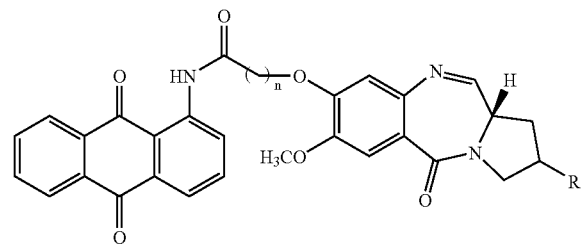

where n is 3 or 4 and R is H or OH.

2. 7-Methoxy-8-[N-(9,10-dihydro-9,10-dioxo-1-anthracenyl)-propane-3-carboxamide]-oxy-(11aS)-1,2,3,11a tetrahydro-5H-pyrrolo [2,1-c][1,4]benzodiazepin-5-one of the formula shown below:

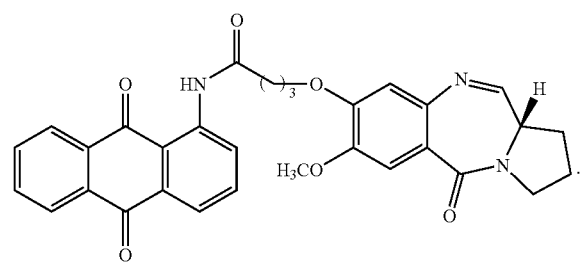

3. 7-Methoxy-8-[N-(9,10-dihydro-9,10-dioxo-1-anthracenyl)-propane-3-carboxamide]-oxy-(4R)-hydroxy-(11aS)-1,2,3,11a tetrahydro-5H-pyrrolo[2,1-c][1,4]benzodiazepine-5-one of the formula shown below:

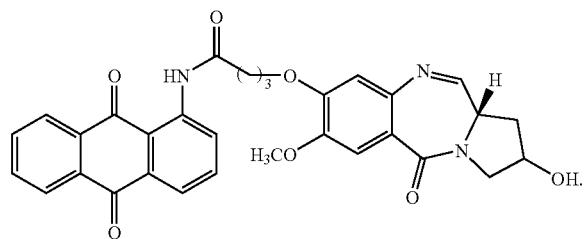

4. 7-Methoxy-8-[N-(9,10-dihydro-9,10-dioxo-1-anthracenyl)-butane-4-carboxamide]-oxy-(11aS)-1,2,3,11a tetrahydro-5H-pyrrolo [2,1-c][1,4]benzodiazepin-5-one of the formula shown below:

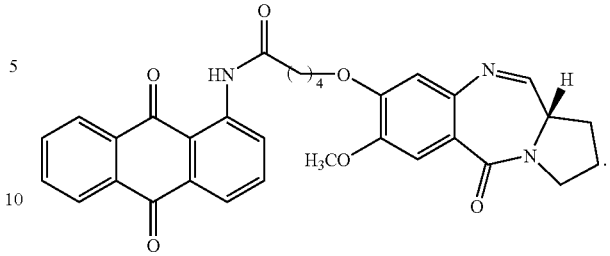

5. 7-Methoxy-8-[N-(9,10-dihydro-9,10-dioxo-1-anthracenyl)-butane-4-carboxamide]-oxy-(4R)-hydroxy-(11aS)-1,2,3,11a tetrahydro-5H-pyrrolo[2,1-c][1,4]benzodiazepine-5-one of the formula shown below:

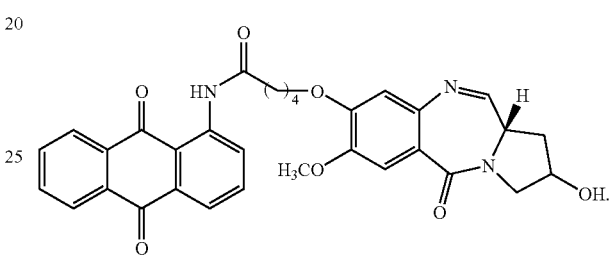

6. A process for the preparation of a compound of formula V wherein n is 3 or 4 and R is H or OH,

V the process comprising:
(a) reacting N-(9,10-dihydro-9,10-dioxo-1-anthracenyl)-1-bromo-alkanamide of formula I with (2S)-N-[4-hydroxy-5-methoxy-2-nitrobenzoyl]pyrrolidine-2-carboxaldehyde diethyl thioacetal of formula II in an aprotic water miscible organic solvent in the presence of a mild inorganic base

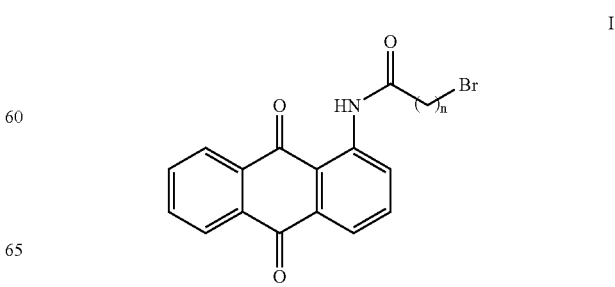

II

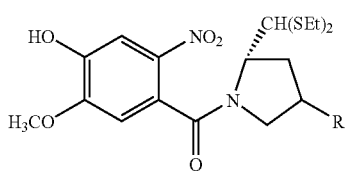

and isolating 2S-N-{4-[N-(9,10-dihydro-9,10-dioxo-1-anthracenyl)-alkane-3-carboxamide]-oxy-5-methoxy-2-nitrobenzoyl}pyrrolidine-2-carbaxaldehyde diethyl thioacetal of formula III so obtained;

III

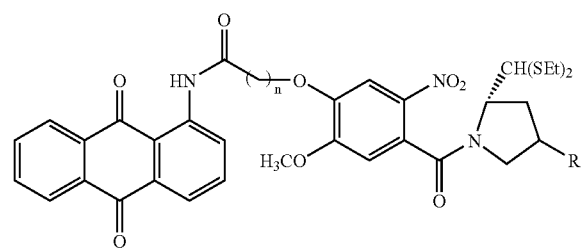

(b) reducing the thioacetal of formula III in presence of organic solvent and isolating 2S-N-{4-[N-(9,10-dihydro-9,10-dioxo-1-anthracenyl)-alkane-3-carboxamide]-oxy-5-methoxy-2-aminobenzoyl}pyrrolidine-2-carbaxaldehyde diethyl thioacetal of formula IV so obtained; and

IV

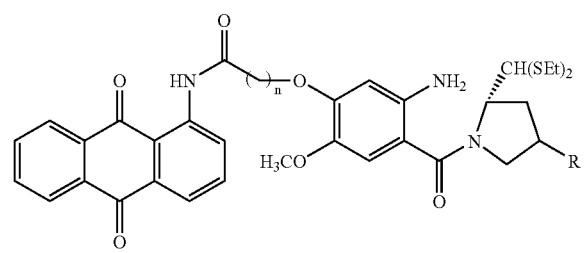

(c) reacting the amino thioacetal of formula IV with a deprotecting agent to give the compound of formula V wherein n is 3 or 4 and R is H or OH.

7. The process of claim 6 wherein the compound of formula I is reacted with the compound of formula II at refluxing temperature and for a period of 48 hours.

8. The process of claim 6 wherein the thioacetal of formula III is reduced using $SnCl_2.H_2O$ in the presence of an organic solvent and at reflux temperature.

9. The process of claim 6 wherein the organic solvent in step (a) comprises acetone.

10. The process of claim 6 wherein the base in step (a) comprises $K_2CO_3$.

11. The process of claim 6 wherein step (b) is carried out in methanol solvent.

12. A method for the treatment of a tumor of a human cancer cell line selected from the group consisting of HT-29, HCT-15, A-549, HOP-62 and SiHA in a subject, comprising administering to the subject a pharmaceutically effective amount of a compound of formula V wherein n is 3 or 4 and R is H or OH

V

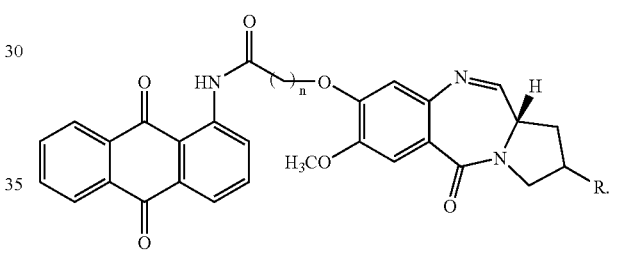

13. The method of claim 12 wherein the subject is a mammal.

14. The method of claim 12 wherein the subject is a human being.

* * * * *

UNITED STATES PATENT AND TRADEMARK OFFICE
CERTIFICATE OF CORRECTION

PATENT NO. : 7,173,026 B2 Page 1 of 1
APPLICATION NO. : 11/024240
DATED : February 6, 2007
INVENTOR(S) : Ahmed Kamal et al.

It is certified that error appears in the above-identified patent and that said Letters Patent is hereby corrected as shown below:

On title page Item [75],

Please delete "B. Khanna Ramesh," and insert -- Bhasker Ramesh Khanna,--

Signed and Sealed this

Tenth Day of April, 2007

JON W. DUDAS
*Director of the United States Patent and Trademark Office*